United States Patent [19]

Jao et al.

[11] Patent Number: 4,543,332

[45] Date of Patent: Sep. 24, 1985

[54] METHOD FOR THE PREPARATION OF SPHERICAL MICROORGANISM CELL AGGREGATES

[75] Inventors: Yun C. Jao, Elkhart; Ivan C. Good, Goshen, both of Ind.

[73] Assignee: Miles Laboratories, Inc., Elkhart, Ind.

[21] Appl. No.: 467,851

[22] Filed: Feb. 24, 1983

Related U.S. Application Data

[63] Continuation-in-part of Ser. No. 362,618, Mar. 29, 1982, abandoned.

[51] Int. Cl.$^4$ .................... C12N 11/02; C12N 11/08; C12N 11/04; C12N 9/90
[52] U.S. Cl. ............................. 435/180; 435/177; 435/182; 435/233
[58] Field of Search ............... 435/94, 174, 177, 178, 435/180, 182, 233

[56] References Cited

U.S. PATENT DOCUMENTS

| | | | |
|---|---|---|---|
| 4,212,943 | 7/1980 | Borglum | 435/180 |
| 4,251,632 | 2/1981 | Chen et al. | 435/180 |

FOREIGN PATENT DOCUMENTS 2137042  7/1971  Fed. Rep. of Germany .

OTHER PUBLICATIONS

Conine, et al., *Drug and Cosmetic Industry*, Apr. 1970.
*Manufacturing Chemist and Aerosol News*, Jun. 1970.

*Primary Examiner*—David M. Naff
*Attorney, Agent, or Firm*—Jerome L. Jeffers; Jennifer L. Skord

[57] ABSTRACT

Spherically shaped bacterial cell aggregates are produced by spheronizing extruded flocculated cells. The cells are flocculated from aqueous medium with a cross-linked polyamine which is the reaction product of an epihalohydrin/polyamine copolymer and a cross-linking agent. Prior to being extruded, a filter cake having 68 to 76 weight percent water is produced by filtration of the flocculated cells, and the filter cake is ground into particles no greater than 60 mesh. Spheronizing is with a plate rotating at a tangential velocity of 4.5 to 12 meters per second within a cylinder containing the plate. Toughness of the spherical aggregates produced can be increased by the addition of a binder after filtration and before extrusion. During spheronizing, fines may be produced. These fines can be recycled by mixing them with the wet filter cake and binder before extrusion.

14 Claims, No Drawings

METHOD FOR THE PREPARATION OF SPHERICAL MICROORGANISM CELL AGGREGATES

BACKGROUND OF THE INVENTION

This application is a continuation-in-part of U.S. application Ser. No. 362,618, which was filed Mar. 29, 1982, and is now abandoned. This disclosure of U.S. application Ser. No. 362,618 is incorporated herein by reference.

The use of enzymes derived from microbial cells to effect specific chemical transformations is well-known. In carrying out such transformations, the cell-free enzyme preparation, ruptured cells or whole cells can be used as the source of the biocatalyst. The free enzyme or cell when used as the source of biocatalyst can be efficiently used in batch-type processes but do not lend themselves to continuous industrial scale processes. The difficulty has led to increased interest in the preparation of various forms of immobilized biocatalysts. A continuous industrial scale process for enzymatic conversion will typically employ a column reactor containing a bed of the immobilized biocatalyst through which flows a solution of material whose biocatalytic conversion is desired.

In the biocatalytic conversion of glucose to fructose, a glucose containing solution is passed over and through the biocatalyst containing bed resulting in the conversion of part of the glucose to fructose. Typically, the biocatalyst is immobilized by flocculation with a cationic or anionic flocculating agent which may be cross-linked by the addition to the reaction medium of a suitable cross-linking agent. The reaction product of the biocatalyst, flocculating agent and cross-linking agent should exhibit high physical strength, as measured by its toughness, so that it will not soften and collapse in use and thereby restrict the flow of liquid through the bed. Solid spherical pelleted particles of the immobilized biocatalyst have certain advantages over those which are simply extruded through sieve plate to form noodle like particles upon drying. For example, such spherical particles flow freely to alleviate material handling problems. In addition, spherical particles can be used to fill a packed column reactor to a greater density of active material than is the case with the non-uniform dried extrudate.

Conine et al report in the April 1970 issue of *Drug and Cosmetic Industry* the preparation of small, solid pharmaceutical spheres by the use of a spheronizing device marketed under the tradename Marumerizer. This article describes the device as comprising a horizontal spinning plate in a stationary cylinder. The plate is milled to create a rough surface which creates friction between itself and the material being spheronized. This device is further described in *Manufacturing Chemist and Aerosol News*, June 1970, in which it is pointed out that the product from the extruder is fed onto the revolving plate where it is disposed against the wall in an annular shape. The extrudate strands are initially broken down by this motion into short lengths, ideally equal to their diameter.

In German AS No. 21 37 042 there is disclosed a method for the spheronization of enzyme compositions, particularly those which are useful in the detergent industry. The compositions to be spheronized are described as being a mixture of 75 to 97% of a solid powder containing the enzyme with 25 to 3% water. The powder may also contain an enzyme stabilizer, a lubricant, a filler and/or a binder. As examples of fillers, this reference mentions inorganic salts, cellulose powder, polyvinyl alcohol and polyvinylpyrrolidone with the last 2 materials also serving as binders, whereas polyethylene-glycols are described as being suitable lubricants. Gelatin, starch decomposition products and other substitutes for enzymes are described as being suitable stabilizers. The enzyme composition is spheronized by extruding it onto the rotating plate of a spheronizing device of the type previously described.

U.S. Pat. No. 4,212,943, issued July 15, 1980, discloses a bacterial cell aggregate having increased hardness which is produced by contacting a mass of bacterial cells with a cross-linking reaction product of (1) glutaraldehyde, cyanuric halide or a combination thereof and (2) a specific cationic polymer obtained by polymerization of an epihalohydrin and an alkylene polyamine. A bacterial cell aggregate of this type having improved hardness characteristics is disclosed in U.S. Pat. No. 4,241,632. This aggregate is prepared by first forming the cell-cross-linker-cationic polymer composition, combining it with particles of a previously prepared and dried aggregate of similar composition, extruding the composition through a die, drying the extrudate and grinding the dried extrudate to the desired particle size.

The resulting particles are non-uniform and have broken jagged edges with irregular surfaces due to the milling process. This type of morphology tends to entrain air bubbles during hydration in glucose syrup causing a floating problem especially when the syrup concentration is higher than 45% on a dry solids basis. This structural characteristic also shows a friable nature which creates undesirable fines during transportation. Fines created are washed off during charging and hydration of the immobilized enzyme in the reactor, and the loss of washed off fines will detrimentally affect the total productivity of the enzyme reactor.

SUMMARY OF THE INVENTION

The present invention is a method for the preparation of spherically shaped bacterial cell aggregates. The method comprises the steps of:

(a) providing an aqueous medium containing viable cells of an enzyme producing microorganism;

(b) introducing the reaction product of a long chain, polyamine, cationic flocculating agent which is an epihalohydrin/polyamine copolymer and a cross-linking agent for said flocculating agent to the aqueous medium to flocculate the cells and form a cell/cross-linked polyamine aggregate;

(c) removing the aggregate from the aqueous medium by sufficient filtration to form a filter cake containing 68 to 76 weight percent water;

(d) grinding the filter cake into particles no greater than 60 mesh;

(e) extruding the filter cake through an orifice, which is approximately the diameter of the spherically shaped cell aggregates to be produced, onto the rotating plate of a spheronizing device which comprises a milled friction plate as rotor situated in a cylinder such that the cylinder provides a stationary side wall for the plate while allowing it freedom to rotate;

(e) rotating the plate at a tangential velocity of 4.5 to 12 meters per second for a time sufficient to cause the extruded aggregate to be disposed against the cylinder wall and be shaped into discrete spherical particles of the cell aggregate; and (f) recovering the spherical particles from the spheronizing device.

DETAILED DESCRIPTION

Typical of the micoorganisms which can be immobilized in the form of tough, spherical aggregates by the method of this invention are those useful in the production of glucose isomerase. Glucose isomerase is an enzyme that can be employed to catalyze the conversion of glucose (dextrose) to fructose (levulose). It is known that fermentation of certain organisms such as *Streptomyces flavoirens, S. echinatur, S. achromogenus, S. albus, S. olivaceus, Actinoplanes missouriensis* and *Bacillus coagulans* in an appropriate nutrient medium results in the production of glucose isomerase. While the detailed description in this specification is directed toward the immobilization of those cells which produce glucose isomerase, the process can be used with various enzyme containing bacterial cells.

The preferred polyamine, cationic flocculating agent used in the aggregation process is commercially available under the trademark BETZ 1180 from Betz Laboratories, Inc., Trevose, Pa. Betz 1180 has a molecular weight of less than one million, contains about 0.288 millimoles of amino groups per gram of solution (based on a ninhydrin assay) and is marketed as a solution containing 30 weight percent solids, based on total solution weight. This material is further described in U.S. Pat. No. 3,915,904 as a water-soluble cationic polymer obtained by the polymerization of an epihalohydrin with an alkylene polyamine having the formula $R_1R_2NRNH_2$ wherein R is a lower alkylene having from 2 to about 6 carbon atoms, and $R_1$ and $R_2$ are each a lower alkyl of from about 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity, and reacting the remaining portion of the epihalohydrin incrementally to obtain the cationic polymer, the temperature of polymerization being from about 60° C. to about 120° C.

The cross-linking agent for the polyamine flocculating agent is typically either glutaraldehyde, a cyanuric halide or a combination thereof. The glutaraldehyde and/or cyanuric halide, which is collectively identified as component (1) is reacted with the polyamine flocculating agent which is identified herein as component (2) at a pH of about 6 to 10 and a temperature of about 0° to 30° C. for about 0.5 to 2.5 hours. The overall cross-linking reaction product contains from about 12 to about 77 weight percent of component (1) and from about 23 to about 88 weight percent of component (2) based on the total weight of active ingredients in components (1) and (2). The glutaraldehyde content of the reaction product is from about 0 to 77 percent and the cyanuric halide content is from about 0 to about 22 percent on a weight basis.

Bacterial cell aggregates are preferably prepared by contacting a mass of bacterial cells in an aqueous medium with the cross-linked reaction product prepared as described above at a pH of about 8 to 9 and a temperature of about 0° to 30° C. for about 0.5 to 1.5 hours. The cross-linked reaction product is employed in an amount such that the bacterial cells are contacted with from about 4.5 to about 60 weight percent of the reaction product based on the dry weight of the cells.

After formation of the bacterial cell aggregate slurry, as above described, it is conveniently placed in a holding or surge tank upstream of filtration apparatus, such as a rotary vacuum filter. The slurry is then filtered to provide a filter cake of moist bacterial cell aggregate. It has been discovered that the filtration must be carefully controlled to provide a filter cake containing 68 to 76 weight percent water if the spheronization step is to work properly. Too high a moisture level in the filter cake causes conveying difficulty through the extruder due to slipping which causes a loss in the desirable compression effect of the extruder on the filter cake. The extrudate so obtained will also cause smearing and lumping problems during spheronization. The overall moisture content can be reduced by adding fines of the immobilized biocatalyst obtained from a previous spheronization run, however, the addition of too many fines such as would be required when more than 76 percent water is present in the filter cake results in a weakened final structure. Conversely, too low a moisture level in the cake tends to create too much friction heat during extrusion which can result in deactivation of the enzyme and can also result in plugging of the die. Furthermore, the extrudate so obtained can easily become shattered during spheronization due to the lack of water to act as a plasticizer. The extrudate is fed from the extruder onto the spinning milled plate where it is disposed against the cylinder wall into an annular or doughnut-like shape with a gradient cross section. The extrudate is initially broken down into short pieces, ideally equal to its diameter, by the friction force on the milled plate and also by the intergranular collision and friction of the moving mass. The characteristic diposition of the material results from the centrifugal force of the spinning of the plate and from the tangential force of the friction between the material and the milled surface. A smooth spinning surface does not allow the extrudate to roll but just to slide to the periphery of the plate. The characteristics of the movement would be different and, therefore, the final shape of the material would not be as uniform and spherical as desired using a smooth plate. The spheronizer is a sphere making machine which can quickly convert immobilized bacterial cell extrudates into small, compact, easily handled spheres. Extruding the aggregate onto the revolving plate causes it to be disposed against the cylinder wall into an annular shape which, during operation of the spheronizer, appears to be twisting like a woven rope. This characteristic disposition of the material is due to the transport of extrudate by the vector resulting from centrifugal and tangential forces toward the periphery of the plate where its residual momentum causes it to rise up the stationary wall and then fall within or over the mass as its momentum dissipates. The extrudate noodles initially break down into pellets and the accelerating and decelerating pellets within the mass form a pattern of velocity gradients which result in the woven rope-like formations. after being broken-down into pellets of short length, the extrudate is shaped into spheres with a diameter which ideally is equal to the diameter of the orifice through which the filter cake of cell aggregate was extruded. This sphere formation is caused by the frictional forces on the milled plate and the interparticle friction of the moving extrudate material. The spheronizing machine used in the following examples is marketed by Fuji Padal Co., Ltd., Osaka, Japan, under the tradename Marumerizer Q-230. This device has a rotor which is 23 centimeters in diameter. Since proper spheronization of the cell aggregate under consideration requires a tangential velocity of 4.5 to 12 and preferably 5 to 9 meters per second (tangential velocity=RPM÷60×π×diameter of plate) the rotation of this particular plate should range from 500 to 1000 revolutions per minute. If the speed of rotation is too great, the plate will simply spin the material away from the plate so drastically and so strongly that the mass will become smashed against the cylinder wall and create undesirable particles, whereas rotating the plate too slowly will not achieve the desired spheronization since there is not provided sufficient momentum within the spinning mass for collision and friction as a down-sizing and spheronizing force. After spheronization, the cell aggregate particles are dried, typically in a fluidized bed dryer.

The enzyme activity of the spheronized cell aggregate particles is roughly equivalent to or higher than that of ground particles indicating that the spheronization procedure is advantageous in terms of providing an aggregate having suitable biocatalytic activity. Aside from providing spherical particles which are inherently easier to handle than those of irregular shape, the aggregates prepared by this process exhibit greater physical toughness and extended enzyme productivity in a reactor. These are the principal advantages of the present invention. Since the dried aggregate can be stored until subsequently needed for use in an enzymatic process, its toughness upon rehydration is a key parameter. In the examples which follow, particle toughness is expressed in relation to resistance to compression as measured by an Instron Universal Tester Model 1102. The load on test cell employed in the tester consists of a transparent acrylic plastic cylinder having an I.D. of 1.720 in. (4.37 cm.) an O.D. of 2.520 in. (6.45 cm.) and a height of 8.5625 in. (21.8 cm.). The bottom portion has a step 0.25 in. (0.635 cm.) thick with an opening of 1.5 in. (3.81 cm.) to form a support for a microfilter. A convenient microfilter is a spinnerette employed in textile spinning having 14,500 openings, each opening being about 0.008 in. (0.2032 mm.). A type 304 stainless steel plunger, 1.693 in. (4.3 cm.) diameter and 5.375 in. (13.66 cm.) long is mounted so as to move coaxially into the above cylinder. Approximate indicia are located along the load cell to show a sample depth of 4 in. (10.17 cm.). Provisions are also made for applying a reduced pressure or vacuum to the bottom of the load cell and for collecting any liquid which passes through the microfilter. If a sample of bacterial cell aggregate is placed in the load cell and pressure is applied to the sample through the plunger, the sample will be compressed. The work needed to compress the sample a given displacement is an indication of the sample's toughness. The test device is used in a rehydration assay procedure for purposes of the examples in this specification.

The rehydration toughness assay procedure is carried out as follows: A 33 weight percent aqueous solution of glucose is adjusted to pH 8.1. A 160 gm. portion of dried bacterial cell aggregate is mixed with 1300 ml. of the glucose solution with gentle agitation at 24° C. for 1 hour. The resulting mixture is drained over a 20 mesh U.S.A. standard testing sieve screen for about 30 seconds. The solids are then resuspended in a fresh portion of the glucose solution and stirred for 5 minutes at 24° C. The resulting slurry is allowed to settle for 5 minutes and then drained as above. The solids are then resuspended in a fresh portion of the glucose solution and stirred for 5 minutes at 24° C. Approximately half of the resulting slurry is then poured into the test cell to a height of 4 in. (10.17 cm.). A reduced pressure or vacuum of 1 in. (2.54 cm.) of mercury is applied to the bottom of the test cell for 3 minutes to suck liquid through the microfilter, and the plunger is then lowered until it just touches the top of the sample. The crosshead on the Instron instrument is attached to the plunger and is set to move downward at a speed of 0.5 in./minute (1.27 cm./minute) and to withdraw automatically at a penetration of 1 in. (2.54 cm.). The recording chart speed is set at 5 in./minute (12.7 cm./minute). The resistance from the enzyme bed against the plunger versus the plunger downward travel distance is recorded on the chart. The resistance force is then expressed as a quadratic function of the plunger travel distance. The toughness of the hydrated enzyme bed represents work done by the plunger against the bed. The higher the endurance of the enzyme bed against compression, the higher the work value and, consequently, the greater the toughness of the aggregate. The toughness of the aggregate is of particular importance in the fixed bed conversion of glucose to fructose because a general life span of a glucose isomerase enzyme bed reactor column is usually longer than 80 days. During this period, the enzyme particles must endure such forces as the weight of the upper enzyme bed layer and the downward dragging force of the syrup. As a result, the aged enzyme bed may collapse to plug up the reactor or may crack to create flow channeling. In either event, the result is detrimental to economical operation of the reactor. However, an enzyme bed with tough particles may remain intact or undergo only minor deformation through the aging period without negatively affecting the physical structure and biochemical performance of the reactor.

It has been discovered that the toughness of the spherical aggregates can be increased by the addition of a binder to the formulation after filtration but before extrusion of the filter cake. A material useful as binder in this formulation should provide intrabinding cohesiveness within a particle but not inter-binding adhesiveness or stickiness such as to cause lumping during spheronization. The desired binder serves as a glue to stick the mass within the particle closely together after drying and, therefore, enhance the toughness of the particle. Examples of suitable binder materials are sodium alginate, Locust bean gum, Xanthan gum, carboxymethylcellulose, kappa carrageenan and Guar gum. In general, suitable binder materials fall into the category of natural gums including seaweed extracts such as alginate and carrageenan, seed gums such as Guar and Locust bean gum; cellulose derivatives such as carboxymethylcellulose, microcrystalline cellulose; and microbial gums such as Xanthan. These are GRAS and often used in food processing.

During the spheronization or drying step, fines of the cell aggregate may be produced. These fines can be recycled by mixing them with the wet filter cake and binder before extrusion. If the amount of filter cake which contains a moisture level in the range of 68 to 76% is taken as 100 weight units, the additional fines which are smaller than 60 mesh on the U.S. sieve series and preferably smaller than 100 mesh, added will be 2.0 to 6.0 units while the gum added as binder should be 0.2 to 0.6 units. The addition of fines can lower the moisture level of the filter cake and provide friction to enhance the spheronizing process without creating undesirable heat during extrusion.

It has been discovered that it is necessary to grind the filter cake prior to extrusion and prior to addition of the gum and/or recycled fines when they are employed. The grinding operation changes the shape and texture of the filter cake from a broad, thin, usually rectangular mass into crumbs with a particle size not greater than 60 mesh. This procedure enhances the homogeneous mixing of gums and recycled fines prior to the extrusion step. Even when recycled fines and a binder are not added, the grinding prevents the formation of too many fines during the spheronizing step so that a tough and uniform product can therefore be obtained through the extrusion, spheronization and drying process.

The method of practicing the present invention is further illustrated by the following examples in which, like the specification, all mesh sizes are on the U.S. standard sieve series.

EXAMPLE I

A culture of a mutant *Streptomyces olivaceus* NRRL 3916 was grown in an agitated aerated fermentor containing an appropriate nutrient medium which is described in U.S. Pat. No. 3,625,828. The resulting fermentor broth containing a mass of bacterial cells was adjusted to pH 8-9 by the addition of appropriate buffering materials.

A solution of polyamine polymer was prepared by diluting 7910 g. of Betz 1180 solution containing 2373 g. of polymer with distilled water to form 27 liters of the diluted solution whose pH was adjusted to 9. A solution of glutaraldehyde was prepared by diluting 12080 ml. of 25 weight percent glutaraldehyde containing 3017 g. of active material with distilled water to form 27 liters of the diluted solution. The 2 solutions were then mixed and distilled water added to form a total of 190 liters. The pH was adjusted to 9 and the reaction allowed to take place at a temperature of about 25° C. for about 0.5 hour to form a reaction product in solution. This solution was added to the above-described fermentor broth in an amount of 15 ml. per gram of dry cell weight to provide 42.5 weight percent total reaction product based on the dry weight of the bacterial cells to form a bacterial cell aggregate. After about 30 minutes of reaction time at 25° C. and pH 8-9, the treated broth containing the bacterial cell aggregate was placed in a holding tank from which it then passed to a rotary vacuum filter. The resulting wet filter cake, which contained 75 weight percent moisture, was divided into 5 portions.

One of the 5 portions was cut into small pieces of about 1 square cm. in a Hobart silent chopper (Model 84145) which were then extruded through a die have 8 1/16 inch (1.59 mm.) diameter openings using a 3:1 compression extruder screw with 100 RPM screw rotation. The resulting extrudate was then dried at 60° C. for 2 to 4 hours and milled through a Homoloid machine with a ⅛ inch opening screen (Model J from the W. J. Fitzpatrick Company) to obtain particles with a size smaller than 16 mesh. Oversize particles resulting from the first mill were recycled and milled until all ground particles were smaller than 16 mesh. The milled particles were then examined for size distribution followed by collecting the desirable size fraction which passed through a 16 mesh U.S. standard testing sieve screen but were retained by a 24 mesh screen. The fines which passed through the 24 mesh screen were collected for further use. The −16+24 mesh fraction so produced was designated as 1A. Its glucose isomerase activity was measured by the assay method set forth in U.S. Pat. No. 3,779,869 to be 500 glucose isomerase units (G.I.U. per gm. or equal to 1$\mu$-mole fructose per minute per gram of enzyme). In addition, the particles' toughness was measured in the previously described Rehydration Toughness Assay Procedure.

Another portion of the moist filter cake was processed exactly the same as the control except the collected particles were −16+48 mesh. This sample was designated as 1B.

A third portion of the filter cake was processed with a Hobart meat grinder through a die having 133 openings of ⅛ inch (3.18 mm.) diameter followed by mixing with recycled fines from the previous batch (particle size smaller than 100 mesh) and Guar gum in a Hobart blender (Model C-100) for 3 to 5 minutes at low speed setting. The composition of the mixture was 1000 gm. filter cake, 60 gm. recycled fines and 2 gm. Guar gum. The mixture was then extruded through a die having sixty 0.04 inch (1 mm.) diameter openings using a 3:1 compression extruder screw with 100 RPM screw rotation. These resulting extrudates ranging in length from 2 to 12 inches were charged into a spheronizing machine having a milled plate 23 cm. in diameter which was milled in the configuration of 2 mm. pitch and 1 mm. in height. The plate with a diameter of 23 cm. was rotated at a speed of 700 RPM to provide a tangential velocity of 8.4 meters per second for 3 minutes whereupon the spheronized extrudate was discharged from the machine through an aperture by centrifugal force. The moisture level of the resulting spheres was 70.6%. A fluidized bed dryer from Aeromatic AG (Model Strea 1) was employed to dry the product with inlet air temperature at 68° C. The final dried spheres contained 8.1% moisture level and were designated as sample 1C. The fourth portion of the moist filter cake was processed exactly the same as that in sample 1C except that the mixture was extruded through a die having sixty 0.028 in. (0.7 mm.) diameter openings and was designated as 1D. The fifth portion of the filter cake was processed in the same manner as that in example 1C except that no gum or recycled fines are added. This sample was designated as 1E.

These 5 samples were subjected to the rehydration toughness assay procedure previously described with the results being tabulated in table Ia.

TABLE Ia

| Sample and Particle Size (mesh) | Enzyme Filter Cake (gm) | *Binder (gm) | Recycled Fines (gm) | Moisture Before Drying (%) | Product Density (g/100 ml) | Activity (GIU/gm) | Increased Toughness (%) |
|---|---|---|---|---|---|---|---|
| 1A (−16+24) | 1000 | 0 | 0 | 73 | 59.8 | 500 | — |
| 1B (−16 +48) | 1000 | 0 | 0 | 73 | 56.4 | 505 | −34.2 |
| 1C (−16+48) | 1000 | 2 | 60 | 70.6 | 80.2 | 499 | 35.5 |
| 1D (−16+48) | 1000 | 2 | 60 | 70.6 | 75.7 | 520 | 25.2 |

TABLE Ia-continued

| Sample and Particle Size (mesh) | Enzyme Filter Cake (gm) | *Binder (gm) | Recycled Fines (gm) | Moisture Before Drying (%) | Product Density (g/100 ml) | Activity (GIU/gm) | Increased Toughness (%) |
| --- | --- | --- | --- | --- | --- | --- | --- |
| 1E (−16+48) | 1000 | 0 | 0 | 71.9 | 69.5 | 520 | 11.7 |

*Binder = Guar gum

The data set out in table Ia indicate that the enzyme activity of the ground as well as the spheronized particles did not show a significant difference; however, the toughness of these particles falls within a wide range. Taking the toughness of sample 1A (−16+24 milled) as a base, the toughness of 1B (−16+48 milled) is 34.2% less, while that of 1C (−16+48 spheronized) and 1D (−16+48 spheronized) and 1E (−16+48 spheronized) are respectively 35.5%, 25.2% and 11.7% greater than that of the control. There is an indication that all of the spheronized samples have a higher value than the ground samples, and that these spheronized wet sample particles had a moisture range of 70.6 to 71.9% prior to the drying process. The total particle size distribution profiles of these samples before screening are set out in table Ib. The data indicate that one of the unique characteristics of the spheronizing process is the production of a higher population in a narrower particle size range. Sample 1C provides 77.5% in the range of −16+24 mesh and same 1D provides 96.7% in the range of −24+48 mesh. However, a higher fraction of undersized fines from the spheronized sample 1E was observed. This sample contained no binder nor were the fines recycled. It should be noted that if a narrow size range is desired from ground particles such as −24+48 mesh, then, a recycle through a milling process is required which results in an undesirably high fraction of fines and the introduction of more heat than is desirable to the process.

TABLE Ib

| Sample | Larger than 16 mesh | −16 +20 | −20 +24 | −24 +28 | −28 +35 | −35 +48 | Smaller than 48 Mesh |
| --- | --- | --- | --- | --- | --- | --- | --- |
| 1A & 1B | 0 | 35.5 | 28 | 15.1 | 8.4 | 4.7 | 8.3 |
| 1C | 0 | 22.2 | 55.3 | 5.5 | 9.2 | 6.5 | 1.3 |
| 1D | 0 | 0.7 | 0.6 | 19.8 | 70.1 | 6.8 | 2 |
| 1E | 0 | 0 | 48 | 12.7 | 4.8 | 4.0 | 30.5 |

EXAMPLE II

This example illustrates the effect of various binders including natural gum and cellulose derivatives, and an inert filler such as microcrystalline cellulose (Avicel from FMC Corporation) on the formation and toughness of the spherical aggregate.

An immobilized glucose isomerase filter cake of 72.9% moisture prepared exactly the same as the cake used in example I was divided into 9 parts and processed as follows: Sample 2A was prepared from 1000 gm. of cake cut into small pieces and mixed with 112 gm. of recycled fines obtained by using the same batch of filter cake and going through a drying step at 60° C. for 2 hours with subsequent milling to a size smaller than 100 mesh and 70 ml. of water in a Hobart blender. The mixture was further extruded, dried, ground, screened and evaluated both biologically and mechanically by the procedure described in the preparation of sample 1A.

Sample 2B was prepared in the same manner as sample 2A except that half of the recycled fines (56 gm.) were replaced by cellulose.

Sample 2C was prepared like sample 1C except that 56 gm. of cellulose, 7 gm. of sodium alginate, 56 gm. of recycled fines and 70 ml. of water were mixed with the ground cake in the blender and the mesh size of dry product evaluated was −16+24. Samples 2D, 2E, 2F, and 2H were prepared exactly the same as sample 2C except the binders used were Locust bean gum, Xanthan gum, carboxymethylcellulose and Guar gum, respectively. Sample 2G was prepared using 8 gm. of kappa carrageenan. Sample 2I was prepared using 7 gm. of Locust bean gum but was extruded through a die with 60 openings of 0.7 mm. diameter and screened to a mesh size of −16+48. The spheronization conditions for samples 2C-2I are set out in table IIb.

Sample 2A, in this case, was used as a control for comparison with the other samples. Sample 2B, which was ground in the manner of 2A, showed almost the same toughness as the control. The moisture before drying and the dry product bulk density of these samples were similar except that the enzyme activity in sample 2B was somewhat diluted by the cellulose. Other samples to which binders were added with subsequent spheronization showed almost the same level of moisture as 2A and 2B; however, their bulk density was in the range of 71.8 to 76.7 gm. per 100 ml. as compared to 64.9 gm. per 100 ml. for the control 2A. The bulk density is the weight of a 100 ml. sample measured from a 100 ml. graduated cylinder. The spheronized particles show a higher bulk density than milled particles due to their spherical shape which enfolds the same amount of mass as the milled counterpart but with less surface area. The toughness of these samples increased at least 25% with the greatest increase being 174%. The spheronization was carried out at a disc rotation speed from 750 to 900 RPM with duration from 2 to 10 minutes. Testing results for the aggregates prepared in this example are shown in table IIa and IIb.

TABLE IIa

| Sample and Particle Size (mesh) | Enzyme Filter Cake (gm) | Cellulose (gm) | *Binder (gm) | Recycled Fines (gm) | Water Added (ml) | (%) Moisture before Drying | Product Bulk Density (g/100 ml) | Activity (GIU/gm) | Increased Toughness (%) |
| --- | --- | --- | --- | --- | --- | --- | --- | --- | --- |
| 2A (−16+24) | 1000 | — | — | 112 | 70 | 68.5 | 64.9 | 571 | — |
| 2B (−16+24) | 1000 | 56 | — | 56 | 70 | 68.0 | 66.7 | 520 | 2.8 |
| 2C (−16+24) | 1000 | 56 | 7 | 56 | 70 | 67.8 | 76.7 | 516 | 174 |
| 2D (−16+24) | 1000 | 56 | 7 | 56 | 70 | 67.8 | 73.2 | 525 | 76 |
| 2E (−16+24) | 1000 | 56 | 7 | 56 | 70 | 67.8 | 75.6 | 568 | 43 |
| 2F (−16+24) | 1000 | 56 | 7 | 56 | 70 | 67.8 | 74.3 | 518 | 65 |
| 2G (−16+24) | 1000 | 56 | 8 | 56 | 70 | 68.6 | 74.9 | 536 | 30 |

TABLE IIa-continued

| Sample and Particle Size (mesh) | Enzyme Filter Cake (gm) | Cellulose (gm) | *Binder (gm) | Recycled Fines (gm) | Water Added (ml) | (%) Moisture before Drying | Product Bulk Density (g/100 ml) | Activity (GIU/gm) | Increased Toughness (%) |
|---|---|---|---|---|---|---|---|---|---|
| 2H (−16+24) | 1000 | 56 | 7 | 56 | 70 | 67.8 | 72.3 | 520 | 75 |
| 2I (−16+48)** | 1000 | 56 | 7 | 56 | 70 | 67.8 | 71.8 | 526 | 25 |

*Binder for each sample:
2C - sodium alginate,
2D and 2I - Locust bean gum;
2E - Xanthan gum;
2F - Carboxymethylcellulose;
2G - Kappa carrageenan;
2H - Guar gum
**2I was extruded through die with sixty 0.7 mm diameter holes

TABLE IIb

| Sample | Spheronization RPM | Duration (min.) |
|---|---|---|
| 2C | 750 | 2 |
| 2D | 750 | 2 |
| 2E | 750 | 3 |
| 2F | 750 | 3 |
| 2G | 750 | 2 |
| 2H | 750 | 4 |
| 2I | 750/900 | 5/5 |

This example illustrates that a variety of binders, including natural gums and cellulose derivatives, can be used along with a filler such as cellulose as part of the composition to enhance the spheronization process. Further, the results indicate that the toughness of all spheronized particles is greater than that of the ground control sample.

EXAMPLE III

This experiment was designed to examine the effect of binders on the toughness of the aggregate with and without the addition of recycled fines. An immobilized enzyme filter cake of 71.9% moisture was divided into 5 parts. Sample 3A was prepared using the same procedure used to prepare sample 2A. Samples 3B, 3C, 3D and 3E were prepared using the procedure used to prepare sample 1C. The formulation of each sample and its physical-biochemical properties along with the spheronizing conditions are set out in tables IIIa and IIIb.

TABLE IIIa

| Sample and Particle Size (mesh) | Enzyme Filter Cake (gm) | Cellulose (gm) | Binder* (gm) | Recycled Fines (gm) | Moisture before Drying % | Product Bulk Density (g/100 ml) | Activity (GIU/gm) | Increased Toughness % |
|---|---|---|---|---|---|---|---|---|
| 3A (−16+24) | 1000 | — | — | 60 | 68.4 | 59.6 | 539 | — |
| 3B (−16+24) | 1000 | — | 6.7 | 56 | 68.1 | 76.5 | 538 | 49 |
| 3C (−16+48) | 1000 | — | 5.3 | — | 71.5 | 76.1 | 542 | 49 |
| 3D (−16+48) | 1000 | — | 2 | — | 71.8 | 76.4 | 540 | 93 |
| 3E (−16+48) | 1000 | 56 | 6.7 | 56 | 64.9 | 77.9 | 492 | 138 |

*Binder for each sample:
3B and 3C - Xanthan gum;
3D - Guar gum;
3E - Sodium alginate.

TABLE IIIb

| Sample | Spheronization RPM | Duration (min) |
|---|---|---|
| 3B | 750 | 4 |
| 3C | 750 | 3 |
| 3D | 750 | 2 |
| 3E | 750 | 4 |

The moisture of all spheronized particles ranged from 64.9 to 71.8%. The bulk density of these spheronized particles ranged from 76.1 to 77.9 gm. per 100 ml. The activity of all the samples was the same, around 540 GIU/gm. except sample 3E (492 GIU/gm.) seemed to be diluted by the addition of cellulose. Toughness of the spheronized samples showed an increased value of 49 to 139% when compared with the control. The spheronization conditions used in this example, as set out in table IIIb, were set at 750 RPM with a duration of 2 to 4 minutes. The effect of binders in the formulation was to enhance the formation of spheres and their toughness even without the addition of recycled fines (3C, 3D).

EXAMPLE IV

In this example, the effect of the use of single and mixed binders on the toughness of the product was studied. A filter cake of 71.2% immobilized enzyme was split into 6 parts. Formulation of each sample is shown in table IVa. Sample 4A, used as control, was prepared using the same procedure as for sample 2A, while the procedure for samples 4B, 4C, 4D, 4E and 4F was the same as that for 2C. The activity and toughness of these particles is set out in table IVa. The toughness of samples 4C and 4D was about 175% higher than that of the control, while that of 4B, 4E and 4F was about 80% higher than the control. The toughness results for samples 4C and 4D showed that there is no cumulative or synergistic effect obtained by using 2 binders as compared to the single system. Results of sample 4B, 4E and 4F indicate the interchangeability between Guar and Locust bean gums possibly due to their similarity in raw material origin and chemical structure. The biocatalytic activity of all the samples was very similar. The bulk density of the control was 63.8 g./100 ml. whereas the spheronized samples showed a density range of 75.8 to 81.2 g./100 ml. The spheronization conditions for these samples are set out in table IVb.

TABLE IVa

| Sample and Particle Size (mesh) | Enzyme Filter Cake (gm) | Binder (gm)* | Recycled Fines (gm) | Moisture before Drying (%) | Product Bulk Density (g/100 ml) | Activity (GIU/gm) | Increased Toughness (%) |
| --- | --- | --- | --- | --- | --- | --- | --- |
| 4A (−16+24) | 1000 | — | 60 | 67.7 | 63.8 | 445 | — |
| 4B (−16+48) | 1000 | 2 | 15 | 70.2 | 81.2 | 452 | 77 |
| 4C (−16+48) | 1000 | 4 | 15 | 70.1 | 75.8 | 440 | 174 |
| 4D (−16+48) | 1000 | 2 + 4 | 15 | 69.6 | 80.7 | 442 | 175 |
| 4E (−16+48) | 1000 | 2 | 15 | 70 | 79.5 | 450 | 80 |
| 4F (−16+48) | 1000 | 1 + 1 | 15 | 70.2 | 80.6 | 449 | 78 |

*Binder for each sample:
4B - Locust bean gum;
4C - Sodium alginate;
4D - 2 gm Locust bean gum + 4 gm Sodium alginate;
4E - Guar gum;
4F - Guar and Locust bean gum.

TABLE IVb

| Sample | Spheronization RPM | Spheronization Duration (min) |
| --- | --- | --- |
| 4B | 700 | 3 |
| 4C | 700 | 3.5 |
| 4D | 800 | 4 |
| 4E | 750 | 3 |
| 4F | 750 | 3 |

EXAMPLE V

This example illustrates the advantage of spheronized particles over the milled counterpart regarding its total available activity expressed in Modified Immobilized Glucose Isomerase Column (MIGIC) assay; cumulative productivity expressed in grams of fructose per gram of enzyme and its half life. Experimental results are summarized in table V.

To prepare the particles, 1 batch of immobilized filter cake with a moisture content of 72.3% was processed the same as the procedure described for sample 1A except that the selected particle size was smaller than 28 but larger than 35 mesh (−28+35). This sample was designated as 5A. A portion of the cake was processed the same as sample 1D except the gum used was Locust bean gum, the amount of recycled fines was 30 gm. and their size range was −28+35. This sample was designated as 5B. Another batch of filter cake with a moisture level of 70.0% was also processed the same as 5A and designated as 6A. A portion of this batch of cake was processed like 5B except the amount of fines used was 60 gm. This sample was designated as 6B. The MIGIC and cumulative productivity assay is carried out as follows:

Principle

This procedure is for assaying immobilized glucose isomerase derived from *Steptomyces olivaceus* var. This assay is intended to give the mean integral rate of glucose isomerase at a 42% fructose conversion. The assay is based on the enzymatic isomerization of a defined glucose substrate to fructose in a column reaction at 60° C. and pH 7.8 (measured at 25° C.) under defined conditions. The conversion rate of glucose to fructose is determined polarimetrically. One Modified Immobilized Glucose Isomerase Column (MIGIC) Unit is defined as that activity which will produce 1μ mole of fructose per minute under the conditions of the assay.

Substrate and Enzyme Preparation

A dual enzyme dextrose syrup containing 71% solids with 95% DE was purchased from Royal Glucose Corn Products. The syrup is diluted to 31% solids, demineralized and supplemented with 50 ppm. magnesium ion, 250 ppm. sulfite and 125 ppm. propyl parahydroxybenzoate. This liquid is used for enzyme preparation and as a substrate for the enzyme system. 25 g. of dry immobilized glucose isomerase is dispensed to a 500 ml. beaker containing 200 ml. of previously prepared syrup. The mixture is allowed to stand for 2 hours. Every half-hour resuspend the glucose isomerase with a stirring rod and readjust to pH 7.8. After 2 hours, the rehydrated glucose isomerase is gently stirred with an overhead stirrer on a hot plate and slowly equilibrated to 60° C.

Assemble and connect jacketed column (1.5×100 cm., from Glenco Scientific, Inc., Houston, TX) to the constant temperature circulating water bath (60° C.±0.1° C.). Place Pyrex glass wool at a depth of 2 cm. above the column outlet. Over the glass wool place approximately 1 cm. of 0.5 mm. glass beads. Into the top of the column add the equilibrated glucose isomerase utilizing a funnel. Allow the hydrated glucose isomerase to settle in the column by gravity. Any isomerase adhering to the inside of the funnel should be washed into the column with additional equilibrated glucose substrate.

With the glucose isomerase in the column, connect the substrate reservoir to the water jacketed column at 60° C. Connect the outlet of the column at 60° C. through the peristaltic pump to an appropriate 3 liter collection vessel.

Assay Procedure

Adjust the substrate flow rate by setting the peristaltic pump from the outlet at a rate of 2 to 4 ml./min. Check the effluent 3 times for the first 24 hours for adjusting the flow rate and then 12 hours thereafter. Sample is allowed to stand at room temperature for 1 hour. Solids concentration of the samples is determined via refractive index. The fractional conversion of glucose to fructose is calculated based on the optical rotation of the glucose substrate and the effluent by polarimetry with confirmation by liquid chromatography to the goal of 42%. A computer program is used to normalize the collected effluent to 42% fructose and corresponding dry solid per day per gram of the enzyme. Extrapolated dry solid per day per gram of enzyme to zero hour can be obtained if the Modified Immobilized Glucose Isomerase Column (MIGIC) assay is conducted for more than 5 days. The MIGIC unit per gram of the enzyme is equal to the dry solid per day per gram of the enzyme at zero hour multiplied by a factor of 1.619. This factor is equal to: (g. dry solid/day)×(day/24 hr.)×(hr./60 min.)×(0.42 g. fructose/g. dry solid)×(Mole fructose/180.16 g. fructose)×($10^6 \mu$ Mole/Mole). The total productivity is defined as the accumulated gram dry solids per gram of enzyme for a certain period of time. It can also be expressed as the accumulated gram fructose per gram of enzyme for the period of time.

Referring to table V, the half life of an enzyme reactor is defined as the period required to decay the activity of the reactor to half of its original activity.

The data in table V reveals that 5B is superior to 5A in GIU/gm. (19.1% higher), MIGIC (59.4% higher) and half life (6.6% longer). It also shows that 6B is superior to 6A by 17% in terms of GIU/gm., 11.2% higher in terms of MIGIC and 60% longer in half life. The cumulative productivity in the reactor for 5B at the end of 43 days when the test was terminated was 36.7% better than that for 5A while that for 6B at the end of 58 days was 28.7% better than 6A. This example illustrates the advantage of spheronized glucose isomerase particles in extended cumulative productivity over the milled control in 2 separate cases.

TABLE V

| Sample and Particle Size (mesh)* | GIU/GM | MIGIC | First Half Life (day) | Cumulative Productivity G Fructose/G Enzyme | Increased Productivity (%) |
|---|---|---|---|---|---|
| 5A (−28+35) | 391 | 101 | 30 | 731.9 (43 days) | — |
| 5B (−28+35) | 466 | 161 | 32 | 1000.8 (43 days) | 36.7 |
| 6A (−28+35) | 498.9 | 88.1 | 33 | 953.8 (58 days) | — |
| 6B (−28+35) | 583.9 | 98 | 53 | 1227.7 (58 days) | 28.7 |

*5A = milled control
5B = spheronized sample
6A = milled control
6B = spheronized sample

What is claimed is:

1. A method for production of spherically shaped bacterial cell aggregates which comprises the steps of:
   (a) providing an aqueous medium containing viable cells of an enzyme producing microorganism;
   (b) introducing a cross-linked polyamine which is the reaction product of a long chain, polyamine, cationic flocculating agent which is an epihalohydrin/polyamine copolymer and a cross-linking agent for said flocculating agent to the aqueous medium to flocculate the cells and form a cell/cross-linked polyamine aggregate;
   (c) removing the aggregate from the aqueous medium by sufficient filtration to form a filter cake containing 68 to 76 weight percent water;
   (d) grinding the filter cake into particles no greater than 60 mesh;
   (e) extruding the filter cake through an orifice, which is approximately the diameter of the spherically shaped cell aggregate to be produced, onto the rotating plate of a spheronizing device which comprises a milled friction plate as rotor situated in a cylinder such that the cylinder provides a stationary side wall for the plate while allowing it freedom to rotate;
   (f) rotating the plate at a tangential velocity of 4.5 to 12 meters per second for a time sufficient to cause the extruded aggregate to be disposed against the cylinder wall and be shaped into discrete spherical particles of the cell aggregate; and
   (g) recovering the spherical particles from the spheronizing device.

2. The method of claim 1 wherein the enzyme producing microorganism is capable of producing glucose isomerase.

3. The method of claim 2 wherein the microorganism is *Streptomyces flavoirens, S. echinatur, S. achromogenus, S. albus, S. olivaceus, Actinoplanes missouriensis* or *Bacillus coagulans.*

4. The method of claim 1 wherein the polyamine flocculating agent is a water soluble cationic polymer obtained by the polymerization of an epihalohydrin with an alkylene polyamine having the formula $R_1R_2NRNH_2$ wherein R is a lower alkylene having from 2 to about 6 carbon atoms and $R_1$ and $R_2$ are each a lower alkyl of from about 1 to about 6 carbon atoms, the mole ratio of epihalohydrin to polyamine being from about 0.60:1 to about 2.7:1, said polymerization comprising reacting with the alkylene polyamine from about 50 to about 90 percent of the amount of epihalohydrin to be polymerized, allowing the reaction to continue until the reaction medium attains a substantially uniform viscosity and reacting the remaining portion of the epihalohydrin incrementally to obtain the cationic polymer, the temperature of polymerization being from about 60° C. to about 120° C.

5. The method of claim 1 wherein the cross-linking agent is glutaraldehyde, a cyanuric halide or a combination thereof.

6. The method of claim 5 wherein the cross-linking agent is glutaraldehyde.

7. The method of claim 1 wherein the reaction product contains from about 23 to about 88 weight percent of the polyamine and from about 12 to about 77 weight percent of the cross-linking agent wherein the cross-linking agent is glutaraldehyde, a cyanuric halide, or a mixture thereof, with the glutaraldehyde content being from about 0 to 77 percent and the cyanuric halide content being from about 0 to 22 percent on a weight basis of the reaction product.

8. The method of claim 1 wherein the cell/cross-linked polyamine aggregate is prepared by contacting a mass of bacterial cells in an aqueous medium of the cross-linked polyamine at a pH of about 8 to 9 and a temperature of about 0° to 30° C. for about 0.5 to 1.5 hours with the cross-linked polyamine being employed in an amount of from about 4.5 to about 60 weight percent of the dry weight of the cells.

9. A method for the production of spherically shaped bacterial cell aggregates which comprises the steps of:
   (a) providing an aqueous medium containing viable cells of an enzyme producing a microorganism;
   (b) introducing the reaction product of a long-chain, polyamine, cationic flocculating agent which is an epihalohydrin/polyamine copolymer and a cross-linking agent for said flocculating agent to the aqueous medium to flocculate the cells and form a cell/cross-linked polyamine aggregate;
   (c) removing the aggregate from the aqueous medium with sufficient filtration to form a filter cake containing 68 to 76 weight percent water;

(d) grinding the filter cake into particles no greater than 60 mesh and adding to the ground filter cake a natural gum, a cellulose derivative or a microbial gum as binder;

(e) mixing the combination of ground filter cake and binder to form a homogeneous mixture and extruding this mixture through an orifice, which is approximately the diameter of the spherically shaped cell aggregate to be produced, onto the rotating plate of a spheronizing device which comprises a milled friction plate as rotor situated in a cylinder such that cylinder provides a stationary side wall for the plate while allowing it freedom to rotate;

(f) rotating the plate at a tangential velocity of 4.5 to 12 meters per second for a time sufficient to cause the extruded mixture to be disposed against the cylinder wall and be shaped into discrete spherical particles; and (g) recovering the spherical particles from the spheronizing device.

10. The method of claim 9 wherein the binder is a natural gum wherein the natural gum is alginate, carrageenan, Guar gum or Locust bean gum.

11. The method of claim 9 wherein the binder is a cellulose derivative wherein the cellulose derivative is carboxymethylcellulose or microcrystalline cellulose.

12. The method of claim 9 wherein the binder is a microbial gum.

13. The method of claim 9 wherein the spherical particles are dried in a fluidized bed dryer after their removal from the spheronizing device, which drying step generates fines of the dried particles, and the fines are added to unextruded, ground filter cake and thoroughly mixed therewith before its extrusion.

14. The method of claim 13 wherein a filter cake having a moisture level of 68 to 76 weight percent is taken as 100 weight units and fines of a size smaller than 60 mesh are added to the ground filter cake in an amount of from 2.0 to 6.0 weight units with the amount of binder added being from 0.2 to 0.6 weight units.

* * * * *